United States Patent [19]

Yasuda

[11] Patent Number: 5,078,684
[45] Date of Patent: Jan. 7, 1992

[54] URETER CORRECTING DEVICE

[75] Inventor: Kenichi Yasuda, Fujinomiya, Japan

[73] Assignee: Terumo Kabushiki Kaisha, Tokyo, Japan

[21] Appl. No.: 459,827

[22] PCT Filed: Sep. 21, 1988

[86] PCT No.: PCT/JP88/00954

§ 371 Date: Jan. 26, 1990

§ 102(e) Date: Jan. 26, 1990

[87] PCT Pub. No.: WO89/02281

PCT Pub. Date: Mar. 23, 1989

[30] Foreign Application Priority Data

Sep. 21, 1987 [JP] Japan .................. 62-236773

[51] Int. Cl.⁵ .................. A61L 29/00; A61L 31/00
[52] U.S. Cl. .................. 604/95; 604/281
[58] Field of Search .......... 604/95, 264, 280, 281; 128/657, 772

[56] References Cited

U.S. PATENT DOCUMENTS

| | | |
|---|---|---|
| 3,867,945 | 2/1975 | Long . |
| 3,868,956 | 3/1975 | Alfidi et al. . |
| 3,890,977 | 6/1975 | Wilson . |
| 4,307,723 | 12/1981 | Finney . |
| 4,497,324 | 2/1985 | Sullivan et al. . |
| 4,503,569 | 3/1975 | Dotter . |
| 4,601,283 | 7/1986 | Chikama ............... 128/4 |
| 4,601,705 | 7/1986 | McCoy ................ 604/95 |
| 4,742,817 | 5/1988 | Kawashima et al. ...... 128/4 |
| 4,758,222 | 7/1988 | McCoy ................ 604/95 |
| 4,776,844 | 10/1988 | Ueda ................. 604/95 |
| 4,790,624 | 12/1988 | Van Hoye et al. ....... 128/4 |
| 4,799,474 | 1/1989 | Ueda .................. 128/4 |
| 4,934,340 | 6/1990 | Ebling et al. ......... 604/95 |
| 4,944,727 | 7/1990 | McCoy ............... 128/657 |
| 4,950,258 | 8/1990 | Kawai et al. ......... 604/281 |

FOREIGN PATENT DOCUMENTS 57-89859 6/1982 Japan .
57-148927 9/1982 Japan .
57-175340 10/1982 Japan .

Primary Examiner—Stephen C. Pellegrino
Assistant Examiner—Ralph A. Lewis
Attorney, Agent, or Firm—Frishauf, Holtz, Goodman & Woodward

[57] ABSTRACT

A ureter correcting device for correcting meandering of a ureter and maintaining a desired shape of the ureter is disclosed. The correcting device is formed by embedding a shape memory alloy member, e.g. a shape memory alloy or resin in a catheter consisting of a rod-like elastic body such as silicone rubber along its longitudinal direction. The catheter further includes warming means for warming the shape memory member. A temperature sensor for detecting the temperature of the shape memory member may be embedded in the catheter as needed. A hollow portion may be formed in the catheter to facilitate bending of the catheter, or side holes or recesses may be formed in the distal end portion of the catheter so as to allow especially the distal end portion to be easily bent.

4 Claims, 2 Drawing Sheets

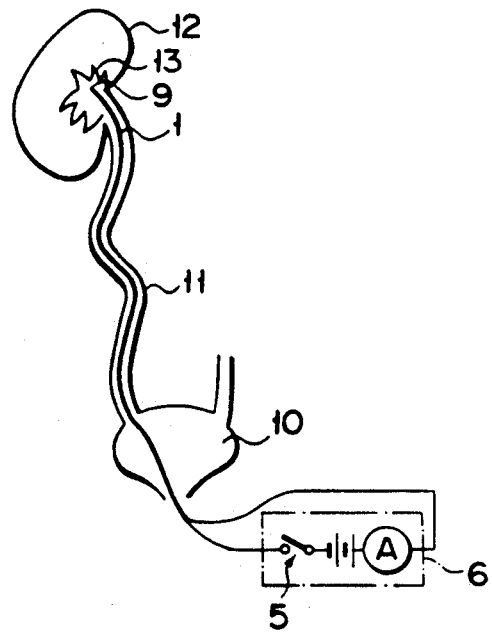
F I G. 4
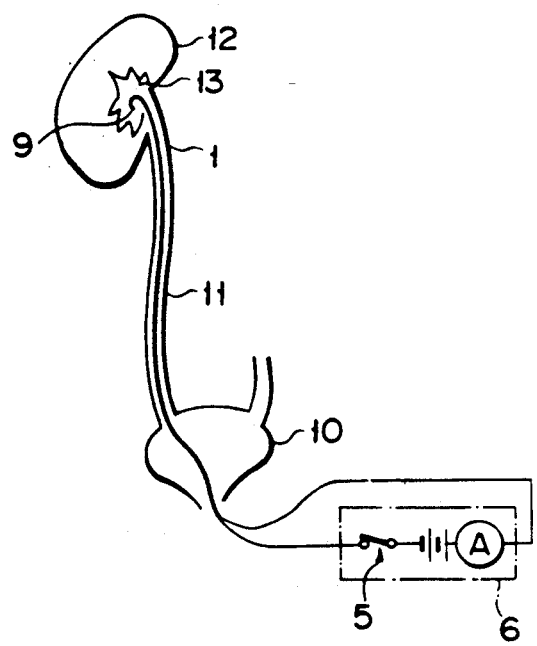
F I G. 5
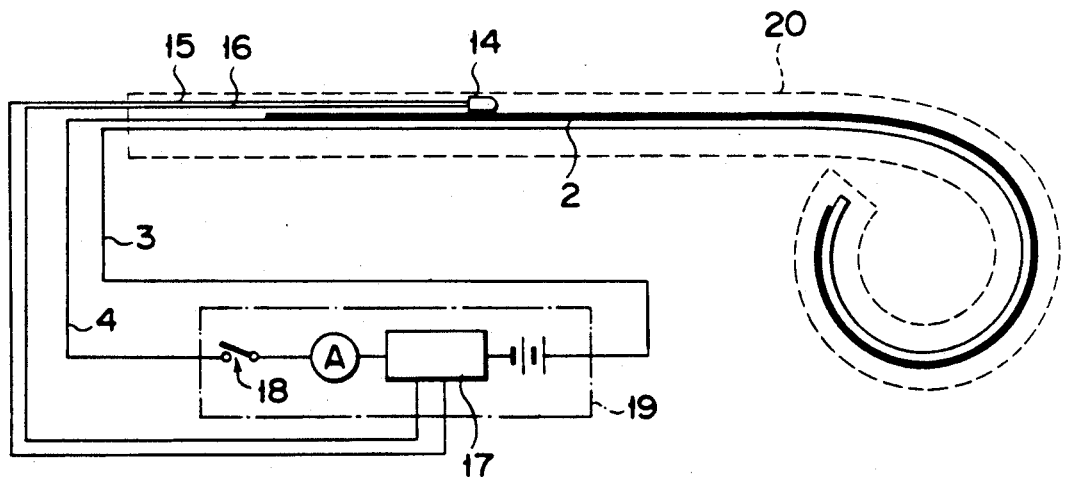
F I G. 6

URETER CORRECTING DEVICE

TECHNICAL FIELD

The present invention relates to a ureter correcting device which is inserted in a ureter to physically correct meandering of the ureter.

BACKGROUND ART

When the ureter of a patient meanders, a medical treatment is performed to correct it. It is rare that meandering of a ureter itself directly poses a physiological problem except for its effect on the structure of the urethra. However, if the ureter greatly meanders, a medical treatment for basic diseases such as urinary tract calculus becomes difficult. For this reason, meandering must be corrected by inserting a ureter correcting device into the ureter of a patient.

A conventional ureter correcting device is designed such that a metal stylet is inserted into a ureter catheter so as to allow the catheter to have a desired straight shape and rigidity.

According to the conventional ureter correcting device, however, since the metal stylet allows the catheter to have rigidity, a urinary tract may be excessively pressurized or damaged by the correcting device upon insertion of the ureter correcting device.

The present invention has been made with the object to provide a ureter correcting device which gives no feeling of being pressurized and which causes no damage to the ureter.

DISCLOSURE OF INVENTION

Recently, an alloy having a shape memory effect has been used in various fields. According to this alloy, when the alloy is heated to a certain temperature range, a desired shape which has been processed in that temperature range is restored regardless of a shape prior to heating. This so-called shape memory alloy utilizes reversibility of martensite transformation. For example, a nickel-titanium alloy is available as a typical shape memory alloy. Since a nickel-titanium alloy can be excellently adapted within a living body, this alloy is expected to be increasingly used in the medical field. Also recently, a shape memory resin having a shape memory effect has been put into practice, and its application in the medical field has been studied. In consideration of these points, in order to improve conventional ureter correcting devices which are unsatisfactory in terms of an insertion feeling and the like, the present inventors have completed the present invention by repeating experiments to utilize shape memory alloys and resins for ureter correcting devices.

According to the present invention, there is provided a ureter correcting device which is inserted in a ureter of a living body to correct meandering of the ureter, characterized by comprising a catheter consisting of a rod-like elastic body, a shape memory member, embedded in the catheter along a longitudinal direction thereof, for restoring a predetermined shape when heated to a predetermined temperature range, and warming means for warming the shape memory member.

According to the ureter correcting device of the present invention, the shape memory member embedded in the catheter is elastically deformed in accordance with the catheter upon insertion, and is rigidly deformed to a desired shape when warmed. More specifically, when the correcting device is inserted into a ureter, since the shape memory member is elastically deformed together with the catheter, the correcting device can be elastically moved along the meandering ureter and can be introduced therein. When the shape memory member is warmed after the distal end of the correcting device reaches a renal pelvis, the phase of the shape memory member is transformed and the member is deformed to a desired shape. Upon deformation of the shape memory member, the catheter is deformed against the elastic force of the ureter, and restores a desired shape to correct meandering of the ureter. After this state is held for a predetermined period of time, warming is stopped and the shape memory member is cooled, and the correcting device is extracted from the ureter.

In order to increase flexibility of the catheter, a hollow portion may be formed in the catheter in its longitudinal direction, more preferably, near the abdominal portion of the catheter (i.e., the inside portion of a bent portion of the catheter) In addition, a plurality of side holes may be formed in that portion to facilitate bending of the distal end portion of the catheter. In place of the hollow portion or the side holes, a plurality of recesses may be formed in the abdominal portion. The shape memory member is preferably constituted by a shape memory alloy or resin. If the shape memory member is constituted by a shape memory alloy, a power supply means is preferably used as the warming means. Moreover, in order to detect the temperature of the shape memory member, a temperature sensor may be embedded near the shape memory member. Note that a unidirectional memory member as well as a bidirectional memory member may be used as the shape memory member.

BRIEF DESCRIPTION OF DRAWINGS

FIGS. 4 and 5 are views each illustrating a state of the ureter correcting device inserted in a ureter; and FIG. 6 is a view illustrating a ureter correcting device according to a second embodiment of the present invention.

BEST MODE OF CARRYING OUT THE INVENTION

Embodiments of the present invention will be described below with reference to the accompanying drawings.

Figure 1:
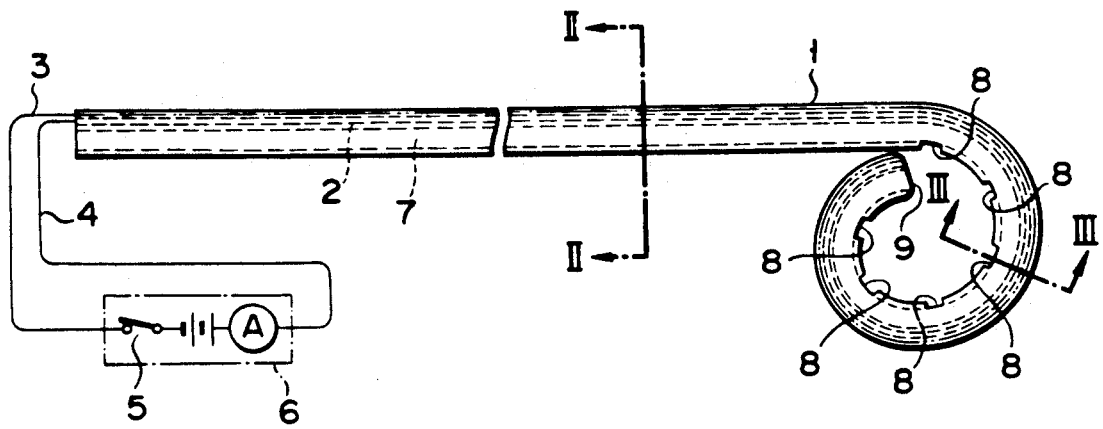
FIG. 1 is a view illustrating a ureter correcting device according to a first embodiment of the present invention.
Figure 2:
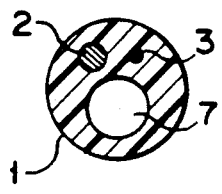
FIGS. 2 and 3 are cross-sectional views respectively taken along lines II—II and III—III of the ureter correcting device according to the first embodiment in FIG. 1.
Figure 3:
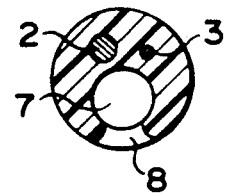

FIG. 1 is a view illustrating a ureter correcting device according to a first embodiment of the present invention. FIGS. 2 and 3 are cross-sectional views of the ureter correcting device according to the first embodiment. FIGS. 4 and 5 are views each illustrating a state of the ureter correcting device inserted in a ureter. A catheter 1 constituting a main part of the ureter correcting device has a rod-like shape and is made of an elastic material having flexibility, thermal stability, and water repellency, e.g., silicone rubber. A plurality of side holes 8 are formed in an abdominal portion near a distal end portion of the catheter 1 along its longitudinal direction so as to facilitate bending of a distal end portion 9 toward the abdominal side. A shape memory alloy wire 2 is embedded in the thicker back side of the catheter 1 (the outside portion of the catheter 1 when it is bent) along its longitudinal direction so as to extend up to near the distal end portion of the catheter 1. The shape memory alloy wire 1 consists of, e.g., a thin wire of a nickel-titanium alloy as a shape memory alloy and has a shape memory effect. The wire has flexibility at a normal body temperature or lower. However, when the wire is heated to a temperature within the range of 37° to 42° C., its phase is subjected to martensite transformation and the wire is deformed into a desired pseudo straight shape suitable for a ureter. In addition, a portion near the distal end of the wire 2 is bent toward the abdominal side of the catheter 1. Both ends of the shape memory alloy wire 2 are connected to a power source unit 6 through leads 3 and 4. A switch 5 is arranged in the power source unit 6.

As shown in FIG. 2, the shape memory alloy wire 2 and the lead 3 are embedded in the back side of the catheter 1. A catheter lumen 7 is eccentrically formed in the catheter, i.e., in the abdominal side of the catheter 1, in its longitudinal direction so as to allow the catheter 1 to be easily bent toward the thinner abdominal side.

An operation of the first embodiment will be described below. FIG. 4 shows a state wherein the catheter 1 is inserted in a ureter 11. More specifically, if the catheter 1 is inserted from a urethra to a predetermined depth, the distal end portion 9 of the catheter 1 reaches a renal pelvis 13 of a kidney 12 after sequentially passing through a urinary bladder 10 and the ureter 11. Although the ureter 11 meanders, since the shape memory alloy wire 2 has flexibility, the wire 2 is elastically deformed along the ureter 11 without damaging it. As a result, the catheter 1 can be conformed to dwell inside in the meandering ureter 11, as shown in FIG. 4.

Subsequently, the switch 5 of the power source unit 6 is closed to supply power to the shape memory alloy wire 2 a temperature within, thereby warming the wire 2 to the range of 37° to 42° C.. As a result, the metal texture of the alloy wire 2 is transformed into a martensite phase to exhibit rigidity against the elastic force of the ureter 11, and the catheter 1 is deformed, as shown in FIG. 5. That is, the entire catheter 11 is deformed into a desired pseudo straight shape, and the distal end portion 9 of the catheter 1 is bent toward the thinner abdominal side in the form of a loop. This bent distal end portion 9 is hooked on the outlet of the renal pelvis 13 so as to prevent the catheter 1 from slipping off from the ureter 11 during power supply. After the power supply state of the catheter 11 is held for a predetermined period of time, the switch 5 is opened to stop the power supply. As a result, the temperature of the alloy wire 2 is decreased to a temperature of 37° C. or lower to restore the flexibility of the catheter 11, and the catheter is extracted.

According to the first embodiment, since the distal end portion 9 of the catheter 1 is distorted in the form a loop during correction, the catheter 1 does not slip off from the ureter 11, and meandering of the ureter 11 can be corrected against the elastic force of the ureter 11.

FIG. 6 is a view illustrating a ureter correcting device according to a second embodiment of the present invention. In the second embodiment, the ureter correcting device of the first embodiment further comprises a temperature sensor so as to control a heating operation for a shape memory alloy wire with high precision. A description of portions of the second embodiment which are identical with those of the first embodiment will be omitted. A shape memory alloy wire 2 is embedded in a catheter 20. A temperature sensor 14 is embedded in the catheter 20 so as to be in contact with part of the alloy wire 2. The temperature sensor 14 is connected to the input side of a current control circuit 17 of a power source unit 19 through leads 15 and 16. The output side of the current control circuit 17 is connected to leads 3 and 4 for supplying electricity to the shape memory alloy wire 2. A current to be supplied to the alloy wire 2 is controlled within a proper range on the basis of a temperature detected by the temperature sensor 14.

When meandering of a ureter is to be corrected by the ureter correcting device having the above-described arrangement, the catheter 20 is inserted into the ureter. When the distal end portion of the catheter 20 reaches the renal pelvis, a switch 18 is closed to supply power to the alloy wire 2. As a result, the alloy is heated and deformed. Since a supply current is controlled on the basis of the temperature of the alloy wire 2 detected by the temperature sensor 14, the temperature of the alloy wire 2 can be held in the desired temperature range of 37° to 42° C. with higher precision.

According to the second embodiment, since the heating temperature of the shape memory alloy wire 2 is controlled with high precision, the rigidity of the catheter 1 during power supply can be stably maintained.

In the above embodiments, a nickel-titanium alloy is employed as a shape memory member. However, the present invention is not limited to this. Similar effects can be obtained by employing other shape memory alloys or resins. For example, a shape memory resin, a polymer ("Norsolex": a trade name of Nippon Zeon Co., Ltd.) obtained by open-ring polymerization of a norbornane polymer upon a Diels-Alder reaction using ethylene and cyclopentadiene, may be employed. In this case, as a warming means for the shape memory resin, a means for supplying a liquid having a temperature higher than a memorized shape restoration temperature, e.g., a physiological saline, is used. The shape memory resin is warmed by supplying a warm liquid and is deformed into a desired shape, thereby correcting meandering of a ureter against its elastic force.

A shape memory member of the present invention is not limited to the bidirectional memory member of the above embodiments, and for example a unidirectional memory member may be employed. More specifically, if a member which has a substantially straight shape as a memorized shape and which is not bent to be hooked on a renal pelvis or the like is employed, the member can be directly extracted upon deformation. Therefore, a unidirectional shape memory member can be used without causing any inconvenience.

In addition, in the above embodiments, a silicone rubber is employed as the catheter. However, the present invention is not limited to this. Similar effects can be obtained by using other elastic materials having thermal stability and water repellency, e.g., neoprene. The lumen 7 of the catheter is not limited to the one in the above embodiments. The lumen may be closed at the distal end portion of the catheter 1. In addition, the side hole 8 need not necessarily communicate with the lumen 7 as shown in FIG. 3. As a means for facilitating bending of the catheter 1, a plurality of recesses may be serially formed at the abdominal side of the distal end portion of the catheter 1 without forming the lumen 7 or the side hole 8.

According to the present invention, since a shape memory member has a low-temperature phase at the time of insertion, the memory member can be flexibly inserted without having the correcting device press against a ureter. On the other hand, the shape memory member obtains a high-temperature phase during correcting upon warming of the member, and is deformed into a desired shape, thus exhibiting rigidity against the elastic force of the ureter. Therefore, a ureter correcting device which causes no feeling of being pressurized during insertion and which causes no damage to the ureter can be provided.

INDUSTRIAL APPLICABILITY

As has been described above, the ureter correcting device of the present invention is used for a medical treatment to physically correct meandering of the ureter of a patient.

I claim:

1. A ureter correcting device which is adapted to be inserted in a ureter of a living body to correct meandering of the ureter, which comprises:

a catheter comprising a rod-like elastic body having a peripheral wall and a hollow portion longitudinally extending along the length thereof, said hollow portion being formed eccentrically with respect to a central axis of said rod-like elastic body to thereby form a thicker side and a thinner side in said peripheral wall of said rod-like elastic body;

a shape memory member embedded in said thicker side of said peripheral wall of said rod-like elastic body and longitudinally extending along the length thereof, said shape memory member being capable of being restored to a memorized shape when heated to a temperature within a predetermined temperature range, said memorized shape being such that said memory shape member is generally straightened except for a distal end portion thereof which is curled towards said thinner side of said peripheral wall of said rod-like elastic body;

power supply means electrically connected to said shape memory member for heating said shape memory member to within said predetermined temperature range to cause said shape memory member to assume its memorized shape; and a temperature sensor embedded in said thicker side of said peripheral wall of said rod-like elastic body for detecting a temperature of said shape memory member.

2. A device according to claim 1, wherein a plurality of side holes are formed in said thinner side of said peripheral wall at a distal end portion of said rod-like elastic body.

3. A device according to claim 1, wherin said shape memory member comprises a shape memory alloy.

4. A device according to claim 1, wherein said temperature sensor is coupled to said power supply means to control the temperature of said shape memory member.

* * * * *